United States Patent

Watanabe

[11] Patent Number: 5,356,289
[45] Date of Patent: Oct. 18, 1994

[54] ORTHODONTIC BRACKET

[76] Inventor: Kazuya Watanabe, Ushio Heights 205, 7-14, Shinden 2-chome, Ichikawa-shi, Chiba-ken, Japan

[21] Appl. No.: 71,486

[22] Filed: Jun. 4, 1993

[30] Foreign Application Priority Data

Sep. 1, 1992 [JP] Japan .................... 4-066700[U]

[51] Int. Cl.$^5$ ................................ A61C 3/00
[52] U.S. Cl. .............................. 433/8; 433/10
[58] Field of Search ............... 433/8, 9, 10, 11, 17

[56] References Cited

U.S. PATENT DOCUMENTS

| 3,043,007 | 7/1962 | Wallshein | 433/8 |
| 3,084,437 | 4/1964 | Neger | 433/11 |
| 3,327,393 | 6/1967 | Brader | 433/11 |
| 3,423,833 | 1/1969 | Pearlman | 433/8 X |
| 3,464,112 | 9/1969 | Silverman et al. | 433/11 |
| 3,964,165 | 6/1976 | Stahl | 433/8 |
| 4,936,774 | 6/1990 | Stoller et al. | 433/17 X |
| 5,174,754 | 12/1992 | Meritt | 433/8 |
| 5,232,361 | 8/1993 | Sachdeva et al. | |
| 5,271,733 | 12/1993 | Chikami et al. | 433/8 X |

Primary Examiner—Gene Mancene
Assistant Examiner—Nicholas D. Lucchesi
Attorney, Agent, or Firm—Flynn, Thiel, Boutell & Tanis

[57] ABSTRACT

In order to provide an orthodontic bracket having no tie wings, capable of removing drawbacks of prior art brackets, in an orthodontic bracket according to the present invention a main body of the bracket is made of shape memory alloy or resin. Further, in lieu of tie wings, there are disposed nail portions for holding an arch wire in a slot of the bracket. Owing to such a construction, the orthodontic force can act thereon with a high efficiency and the size of the bracket can be reduced. In addition, since the tie wings are unnecessary, accidents due to a cut end of a ligature wire are reduced.

3 Claims, 2 Drawing Sheets

ORTHODONTIC BRACKET

FIELD OF THE INVENTION

The present invention relates to improvement of an orthodontic bracket.

BACKGROUND OF THE INVENTION

FIG. 5 shows a prior art orthodontic bracket. In the figure reference numeral 1 indicates a main body of the bracket, which is made of a rigid substance having a fixed form against orthodontic force transmitted through an arch wire. Tie wings 3 necessary at ligating the arch wire are disposed on this bracket.

However in such a prior art bracket structure having tie wings, since the tie wings 3 are attached on occlusal and gingival sides of the main body of the bracket 1, food residue stagnates often inside the tie wing, which gives rise to gingivitis or halitosis.

Further there was often danger that a finger was wounded by a cut end of a ligature wire while ligating the wire against the tie wings 3, which led to inside infection among medical workers.

In addition, the tie wings on the occlusal side collided sometimes with opposing teeth and also for teeth in the course of eruption the tie wings on the gingival side were brought into contact with gingiva, which prevented to mount the bracket at a suitable position.

OBJECT OF THE INVENTION

The object of the invention is to provide an orthodontic bracket, which removes the drawbacks of the prior art techniques described above owing to the fact that the tie wings are made unnecessary.

SUMMARY OF THE INVENTION

In order to achieve the above object, the orthodontic bracket according to the present invention is characterized in that a plurality of nail portions for holding an arch wire in a slot of the bracket are formed on a main body of the bracket made of shape memory alloy or resin.

When the arch wire is mounted on or dismounted from the bracket, this is carried out by utilizing elasticity of the slot itself while thrusting the arch wire on the nail portions.

DETAILED DESCRIPTION

Figure 1:
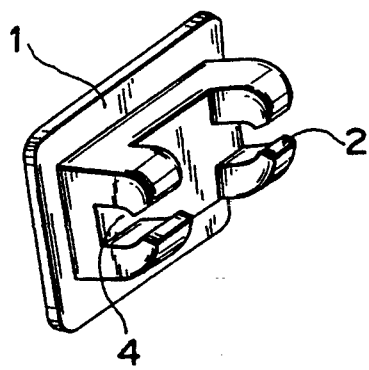
FIG. 1 is a perspective view showing an embodiment of the present invention.

Hereinbelow an embodiment of the present invention indicated in the drawings will be explained.

FIG. 1 shows the embodiment of the orthodontic bracket according to the present invention, in which a main body 1 of the bracket is made of shape memory alloy or resin. As a result, the bracket not only transmits orthodontic force to teeth through an arch wire but also has a function of generating orthodontic force by itself.

Next nail portions 2 for holding an arch wire in a slot 4 of the bracket are newly disposed. Owing thereto, since tie wings disposed on a prior art orthodontic bracket for ligating the arch wire are eliminated, it is possible to reduce the size of the main body 1 of the bracket and it is easier to keep the teeth of a patient under orthodontic treatment clean. Further, owing to the nail portions, since it is possible to hold the arch wire in the slot of the bracket without ligating it, danger that a finger is wounded by a cut end of a ligature wire is reduced, which is useful for preventing inside infection among medical workers.

Figure 2:
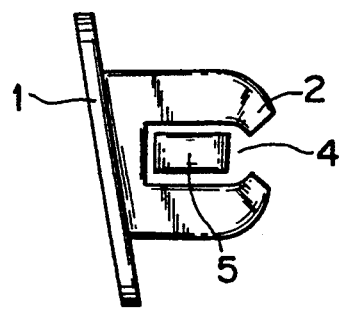
FIG. 2 is a cross-sectional view indicating a state of use of the embodiment indicated in FIG. 1.
Figure 3:
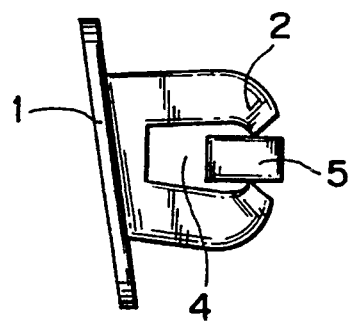
FIG. 3 is a cross-sectional view indicating another state of use of the embodiment indicated in FIG. 1.

FIG. 2 shows a state where the arch wire 5 is mounted in the slot 4 of the bracket in the embodiment described above. FIG. 3 shows a state where the arch wire 5 is being mounted or dismounted on from the slot 4 of the bracket. As clearly seen from the last figure, the bracket is designed so as to be deformed by elasticity of itself so that the arch wire 5 can get over the nail portions 2, when the arch wire is mounted or dismounted.

Figure 4:
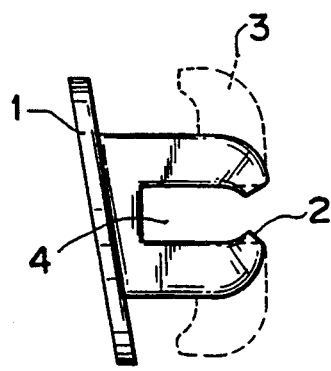
FIG. 4 is a diagram showing the structure of the bracket according to the present invention, compared with prior art one, in cross-section.
Figure 5:
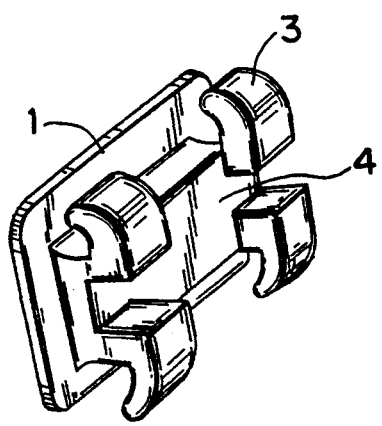
FIG. 5 is a perspective view of a prior art orthodontic bracket having tie wings.

FIG. 4 shows the bracket according to the present invention, compared with prior art one, in cross-section, where dotted lines represent conventional tie wings 3. According to the present invention, the nail portions 2 are newly disposed instead thereof. Concerning the shape and the number of nail portions, there is no special restriction, if they can hold the arch wire.

As explained above, according to the present invention, since the main body of the bracket is made of shape memory alloy or resin, the bracket itself generates orthodontic force together with the arch wire and in this way more efficient orthodontic force can be obtained than by the prior art bracket.

Further, since the nail portions are disposed in lieu of the conventional tie wings, the size of the bracket can be reduced. Furthermore, since the arch wire is held in the slot of the bracket without ligating it, it is possible to reduce remarkably danger that a finger is wounded by a cut end of a ligature wire.

What is claimed is:

1. In an orthodontic bracket which includes a main body made of a shape memory alloy; and a plurality of pairs of longitudinally elongated hold members formed on said main body so as to define a slot which extends between said hold members of each said pair; the improvement comprising wherein each said hold member has at an outer end thereof a nail portion which projects only in a direction into said slot to hold an arch wire in said slot of the bracket so that an exit of the arch wire from said slot is resisted by said nail portions, said bracket being free of tie wings projecting from said hold members in a direction away from said slot for ligating the arch wire.

2. An apparatus comprising an orthodontic bracket which is made of a shape memory alloy and which includes a main portion and first and second pairs of nail portions projecting outwardly from said main portion in a first direction and spaced from each other in a second direction substantially perpendicular to said first direction, the nail portions of each said pair being spaced from each other in a third direction substantially perpendicular to each of said first and second directions, each said nail portion having a dimension in said first direction which is greater than dimensions thereof in each of said second and third directions, the nail portions of each said pair having end portions which are remote from said main body and which have a first distance therebetween, and having further portions between said end portions and said main body which have therebetween a second distance greater than said first distance, each said nail portion of each said pair being free of a tie wing projecting away from the other nail portion of the pair and shaped to have an arch wire ligated thereon.

3. An apparatus according to claim 2, wherein said main portion includes an approximately platelike portion which extends approximately parallel to said second direction and at an angle to said first direction.

* * * * *